United States Patent [19]

Hermecz et al.

[11] Patent Number: 4,803,274
[45] Date of Patent: Feb. 7, 1989

[54] NORFLOXACIN INTERMEDIATE

[75] Inventors: István Hermecz; Géza Kereszturi; Lelle Vasvári; Ágnes Horváth, all of Budapest; Mária Balogh, Dunakeszi; Gábor Kovács, Budapest, all of Hungary; Zoltán Mészáros, deceased, late of Budapest, Hungary, by Márta Mészáros, Márta Mészáros née Bölöni, heiresses; Péter Ritli, Budapest, Hungary; Judit Sipos, Budapest, Hungary; Anikó Pájor, Budapest, Hungary

[73] Assignee: Chinoin Gyogyszer es Vegyeszeti Termekek Gyara Rt., Budapest, Hungary

[21] Appl. No.: 105,298

[22] Filed: Aug. 7, 1987

[30] Foreign Application Priority Data

Dec. 9, 1985 [HU] Hungary ................ 4693/85

[51] Int. Cl.$^4$ ............... C07F 5/02; C07D 215/56
[52] U.S. Cl. ........................... 546/13; 546/156
[58] Field of Search ........................... 546/13

[56] References Cited

U.S. PATENT DOCUMENTS 4,182,880 1/1980 Watanabe et al. ............ 546/13

OTHER PUBLICATIONS

Chem. Abstracts, vol. 102, (7), abst. No. 102:62272-y, Feb. 18, 1985.
Chem. Abstracts 103:123491p (1985).
Chem. Abstracts 105:153293j (1986).
Chem. Abstracts Formula Index 1982-1986, p. 13441F and p. 7575F.

Primary Examiner—Alan L. Rotman
Attorney, Agent, or Firm—Herbert Dubno; Jonathan Myers

[57] ABSTRACT

The invention relates to a process for the preparation of compounds of the Formula I

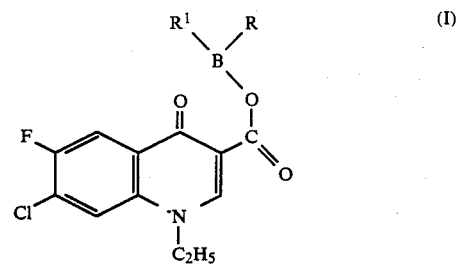

(wherein R and $R^1$ stand for an aliphatic acyloxy group comprising 2-5 carbon atoms and optionally substituted by halogen or for an aromatic acyloxy group comprising 7-11 carbon atoms), which comprises reacting a compound of the general Formula II

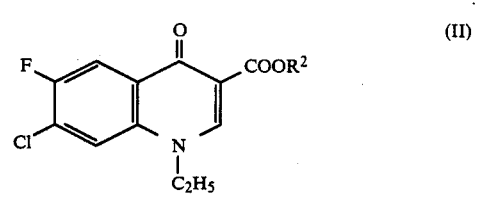

(wherein $R^2$ stands for hydrogen or alkyl comprising 1-4 carbon atoms) with a boron derivative of the Formula III

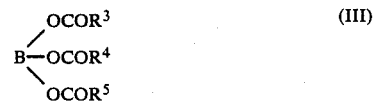

(wherein $R^3$, $R^4$ and $R^5$ stand for an alkyl group comprising 1-4 carbon atoms and optionally substituted by halogen or for an aryl group comprising 6-10 carbon atoms).

The new compounds of the general Formula I are useful pharmaceutical intermediates.

2 Claims, No Drawings

NORFLOXACIN INTERMEDIATE

FIELD OF THE INVENTION

This invention relates to new intermediates useful in the preparation of Norfloxacin. More particularly it is concerned with new anhydrides of 1-ethyl-6-fluoro-7-chloro-4-oxo-1,4-dihydro-quinoline-3-carboxylic acid and boric acids and a process for the preparation thereof.

BACKGROUND OF THE INVENTION

It is known that ethyl-1-ethyl-6-fluoro-7-chloro-4-oxo-1,4-dihydro-quinoline-3-carboxylate (Journal of Medicinal Chemistry 23, 1358 (1980); Japanese patent specification No. 80 33,453) is an intermediate useful in the preparation of 1-ethyl-6-fluoro-7-substituted-4-oxo-1,4-dihydro-quinoline-3-carboxylic acids having antibacterial effect (Ann. Microbiol, Paris 1981, 132A, 267; Journal of Medicinal Chemistry 1980, 23, 1358; Pathol. Biol. 1982, 30, 394; Cyo Yakuri, 1983, 25, 475; Pathol. Biol. 1983, 31, 501; Antimicrob. Agents Chemother. 1980, 17, 103; 1981, 19, 188; 1981, 20, 265; C. R. Scances Acad. Sci., Ser. 3, 1981, 292, 37).

The latter compounds can be prepared in two steps by reacting ethyl-1-ethyl-6-fluoro-7-chloro-4-oxo-1,4-dihydro-quinoline-3-carboxylate with a cyclic amine at a temperature above 100° C. in the presence of a solvent for several hours and subjecting the ethyl-1-ethyl-6-fluoro-7-substituted-4-oxo-1,4-dihydro-quinoline-3-carboxylate thus obtained to hydrolysis; the order of succession of the said two steps can be changed, if desired (Japanese patent specification Nos. 79,138,582 and 80,33,453; Belgian patent specification Nos. 863,429; 870,917; 879,106 and 890,223; DOS No. 2,840,910 and French patent publication No. 2,424,919).

The above processes are accompanied by several drawbacks. The reaction time used is long. Moreover the halogen/amine group replacement reaction is not selective and in addition to the desired chloro/amine reaction in position 7 also a fluoro/amine exchange in position 6 takes place to a considerable extent.

DESCRIPTION OF THE INVENTION

It has been found that the selectivity of the desired halogen/amine replacement reaction in position 7 can be increased significantly by reacting a cyclic amine with an anhydride of the Formula I (wherein R and $R^1$ stand for an aliphatic acyloxy group comprising 2–5 carbon atoms and optionally substituted by halogen or for an aromatic acyloxy group comprising 7–11 carbon atoms). A further advantage of this process is that the reaction time is significantly shorter.

According to the present invention there is provided a process for the preparation of compounds of the Formula I

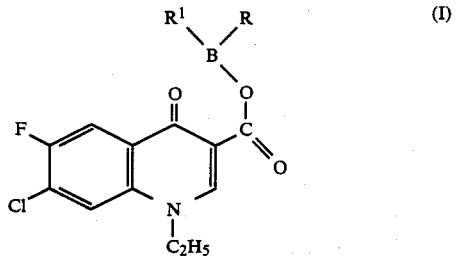

(wherein R and $R^1$ stand for an aliphatic acyloxy group comprising 2–5 carbon atoms and optionally substituted by halogen or for an aromatic acyloxy group comprising 7–11 carbon atoms), which comprises reacting a compound of the Formula II

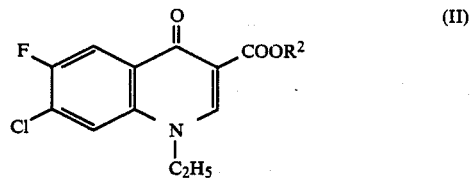

(wherein $R^2$ stands for hydrogen or alkyl comprising 1–4 carbon atoms) with a boron derivative of the Formula III

(wherein $R^3$, $R^4$ and $R^5$ stand for an alkyl group comprising 1–4 carbon atoms and optionally substituted by halogen or for an aryl group comprising 6–10 carbon atoms).

The reaction of the quinoline-3-carboxylic acid of the Formula II and the boron derivative of the Formula III can preferably be carried out in an optionally halogenated organic carboxylic acid—which may also contain the corresponding acid anhydride—at a temperature between 0° and 200° C. The compound of the Formula I thus formed precipitates from the reaction mixture either spontaneously or under cooling and can be separated e.g. by filtration.

The reaction may however also be carried out in an other solvent (e.g. sulfoxide, amides, pyridine, aromatic hydrocarbons), if desired.

The boron derivatives of the Formula III can be used in a molar ratio of 1–50 moles related to 1 mole of the quinoline-3-carboxylic acid derivative of the Formula II.

Further details of the present invention are to be found in the following Examples without limiting the scope of protection to the said Examples.

EXAMPLE 1

A mixture of 9.3 g of boric acid and 70 g of propionic anhydride is stirred at 100° C. for 15 minutes whereupon the reaction mixture is heated to the boiling point. After half an hour the temperature is lowered to 110° C. and 29.8 g of ethyl-1-ethyl-6-fluoro-7-chloro-4-oxo-1,4-dihydro-quinoline-3-carboxylate are added. The reaction mixture, which turns to a thick suspension within some minutes, is stirred at 110° C. for 2 hours, then cooled to room temperature and diluted with 300 ml of water. The reaction mixture is cooled and the precipitated crystals are filtered. Thus 41.5 g of (1-ethyl-6-fluoro-7-chloro-4-oxo-1,4-dihydro-3-quinoline-carboxylate-$O^3,O^4$-)-bis-(propanoato-O)-boron are obtained, yield: 97.7%; Mp.: 252° C. (decomposition).

Analysis for the Formula $C_{18}H_{18}BFClNO_7$: calculated: C=50.79%, H=4.26%, N=3.29%; found: C=50.94%, H=4.15%, N=3.41%.

EXAMPLE 2

A mixture of 46.3 g of boric acid and 345 g of propionic anhydride is stirred at 100° C. for 15 minutes whereupon the reaction mixture is heated to boiling. After half an hour the reaction temperature is lowered to 110° C. and 134.5 g of 1-ethyl-6-fluoro-7-chloro-4-oxo-1,4-dihydro-quinoline-3-carboxylic acid are added. The reaction mixture is stirred at 110° C. for 2 hours and cooled under 10° C. The reaction mixture is diluted with 150 ml of water and allowed to crystallize in a refrigerator overnight. Next morning the precipitated crystals are filtered, washed with water and dried in vacuo. Thus 208.6 g of (1-ethyl-6-fluoro-7-chloro-4-oxo-1,4-dihydro-3-quinoline-carboxylato-$O^3,O^4$)-bis-(propanoato-O)-boron are obtained, yield: 98%. The product melts at 269° C. (decomposition). A mixture of the product-formed with any amount of the compound prepared according to Example 1 shows no melting point depression.

EXAMPLE 3

A mixture of 9.3 g of boric acid and 54.1 g of acetic anhydride is heated at 110° C. for 30 minutes. The reaction mixture is cooled to 80° C. and 29.8 g of ethyl-1-ethyl-6-fluoro-7-chloro-4-oxo-1,4-dihydro-quinoline-3-carboxylate are added. The reaction mixture is stirred at 110° C. for 2 hours, cooled below 10° C. and diluted with 100 ml of water. The cooled reaction mixture is allowed to crystallize in a refrigerator overnight. Next morning the precipitated crystals are filtered, washed with water and dried. Thus 33.5 g of (1-ethyl-6-fluoro-7-chloro-4-oxo-1,4-dihydro-3-quinoline-carboxylato-$O^3,O^4$)-bis(acetato-O)-boron are obtained. Yield: 84.4%. The product decomposes at 274° C.

Analysis for the Formula $C_{16}H_{14}FClBNO_7$: calculated: C=48.34%, H=3.54%, N=3.52%; found: C=48.48%, H=3.43%, N=3.57%.

EXAMPLE 4

2.74 g of boric acid and 22.6 g. of acetic acid anhydride are reacted in the presence of 2 mg of zinc chloride. The boric acid is gradually added to the acetic acid anhydride while the reaction temperature rises to 80° C. The temperature of the reaction mixture is then slowly raised to 110° C. and 8.79 g. of ethyl-1-ethyl-6-fluoro-1,4-dihydro-7-chloro-4-oxo-3-quinoline-carboxylate are added, which had been previously dissolved in 18 ml. of hot 96% by W/V acetic acid. The orange-red clear solution is stirred for 2 hours at 110° C. and then allowed to cool. The precipitated crystals are filtered and washed several times with water and once with methanol and dried. 10.8 g (92.1%) off-white (1-ethyl-6-fluoro-7-chloro-1,4-dihydro-4-oxo-3-quinoline-carboxylate-$O^3,O^4$)-bis(acetato-O)-boron are obtained, decomposing at 273° C.

Analysis for the formula $C_{16}H_{14}BClFNO_7$: calculated: C=48.35%, H=3.55%, N=3.52%; found: C=48.2%, H=3.5%, N=3.2%.

What we claim is:

1. A compound of the Formula (I)

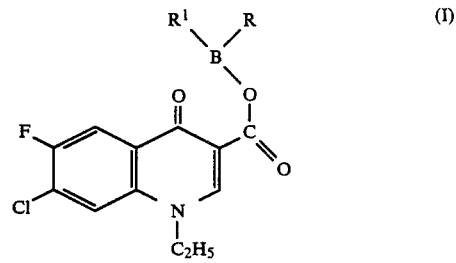

wherein R and $R^1$ are each $C_2$ and $C_5$ alkanoyloxy or benzoyloxy.

2. The compound of the Formula (I) defined in claim 1 wherein R and $R^1$ are each acetoxy, propionyloxy, or benzoyloxy.

* * * * *